US006297428B1

(12) United States Patent
Guilley et al.

(10) Patent No.: US 6,297,428 B1
(45) Date of Patent: Oct. 2, 2001

(54) METHOD FOR INDUCING VIRAL RESISTANCE INTO A PLANT

(75) Inventors: Hubert Guilley, Berstett; Gerard Jonard, Strasbourg; Ken Richards, Pfulgriesheim; Salah Bouzoubaa; Claudine Bleykasten-Grosshans, both of Strasbourg, all of (FR); Guy Weyens, Beersel; Marc Lefebvre, Jodoigne, both of (BE)

(73) Assignee: SES Europe N.V./S.A. (BE)

( * ) Notice: Subject to any disclaimer, the term of this patent is extended or adjusted under 35 U.S.C. 154(b) by 0 days.

(21) Appl. No.: 09/242,216

(22) PCT Filed: Aug. 19, 1997

(86) PCT No.: PCT/BE97/00092

§ 371 Date: Feb. 8, 1999

§ 102(e) Date: Feb. 8, 1999

(87) PCT Pub. No.: WO98/07875

PCT Pub. Date: Feb. 26, 1998

(30) Foreign Application Priority Data

Aug. 19, 1996 (EP) .................................................. 96870106

(51) Int. Cl.[7] .............................. C12N 5/04; C12N 15/82; C12N 15/90; A01H 5/00; A01H 5/10

(52) U.S. Cl. .......................... 800/280; 435/417; 435/419; 435/468; 800/287; 800/301; 800/315; 800/317.2

(58) Field of Search .................................... 435/69.1, 410, 435/419, 468, 417; 536/23.72; 800/278, 279, 280, 287, 288, 295, 298, 301, 315, 317.2, 520

(56) References Cited

FOREIGN PATENT DOCUMENTS

WO 92/13159 9/1991 (WO) ............................ C12N/15/82

OTHER PUBLICATIONS

Lauber et al, J. Gen. Virol., vol. 79, pp. 385–393, 1998.*

Virology 189, 40–47 (1992) Efficient Cell–to–Cell Movement of Beet Necrotic Yellow Vein Virus Requires 3'Proximal Genes Located on RNA 2, D. Gilmer et al.

Plant Cell Reports (1995) Genetically engineered resistance to potato virus X in four commercial potato culitvars, Huimin Xu et al.

Proc. Natl. Acad. Sci. USA vol. 91, pp. 10310–10314, Oct. 1994, Plant Biology Disruption of virus movement confers broad–spectrum resistance against systemic infection by plant virus with a triple gene block.

* cited by examiner

*Primary Examiner*—Elizabeth F. McElwain
*Assistant Examiner*—Ashwin D. Mehta
(74) *Attorney, Agent, or Firm*—Knobbe, Martens, Olson & Bear LLP

(57) ABSTRACT

The present invention concerns a method for inducing resistance to a virus comprising a TGB3 sequence with the proviso that it is not the potato virus X, into a plant cell or plant, comprising the following steps: preparing a nucleic acid construct comprising a nucleic acid sequence corresponding to at least 70% of the nucleic acid sequence of TGB3 of said virus or its corresponding cDNA, being operably linked to one or more regulatory sequence(s) active in a plant, transforming a plant cell with the nucleic acid construct, and possibly regenerating a transgenic plant from the transformed plant cell. The present invention is also related to the plant obtained.

26 Claims, 8 Drawing Sheets

SEQ ID NO.1

FIG. 6

```
1/1                                     31/11
ATG GTG CTT GTG GTT AAA GTA GAT TTA TCT AAT ATT GTA TTG TAC ATA GTT GCC GGT TGT
M   V   L   V   V   K   V   D   L   S   N   I   V   L   Y   I   V   A   G   C
61/21                                   91/31
GTT GTT GTC AGT ATG TTG TAC TCA CCG TTT TTC AGC AAC GAT GTT AAA GCG TCC AGC TAT
V   V   V   S   M   L   Y   S   P   F   F   S   N   D   V   K   A   S   S   Y
121/41                                  151/51
GCG GGA GCA ATT TTT AAG GGG AGC GGC TGT ATC ATG GAC AGG AAT TCG TTT GCT CAA TTT
A   G   A   I   F   K   G   S   G   C   I   M   D   R   N   S   F   A   Q   F
181/61                                  211/71
GGG AGT TGC GAT ATT CCA AAG CAT GTA GCC GAG TCC ATC ACT AAG GTT GCC ACC AAA GAG
G   S   C   D   I   P   K   H   V   A   E   S   I   T   K   V   A   T   K   E
241/81                                  271/91
CAC GAT GTT GAC ATA ATG GTA AAA AGG GGT GAA GTG ACC GTT CGT GTT GTG ACT CTC ACC
E   D   V   D   I   M   V   K   R   G   E   V   T   V   R   V   V   T   L   T
301/101                                 331/111
GAA ACT ATT TTT ATA ATA TTA TCT AGA TTG TTT GGT TTG GCG GTG TTT TTG TTC ATG ATA
E   T   I   F   I   I   L   S   R   L   F   G   L   A   V   F   L   F   M   I
361/121                                 391/131
TGT TTA ATG TCT ATA GTT TGG TTT TGG TAT CAT AGA TAA
C   L   M   S   I   V   W   F   W   Y   H   R   *
```

METHOD FOR INDUCING VIRAL RESISTANCE INTO A PLANT

This is the U.S. national phase under 35 U.S.C. § 371 of International Application PCT/BE97/00092, filed Aug. 18, 1997.

1. Field of the invention

The present invention is related to a method for inducing viral resistance into a cell and plant, especially BNYVV-resistance into a sugar beet cell and plant and the viral resistant cell and plant obtained.

2. Background of the invention and state of the art

The widespread viral disease of the sugar beet plant (*Beta vulgaris*), called Rhizomania is caused by a furovirus (as used herein, the term "furovirus" is used in the sense that term was used at the time of filing, which was prior to the taxonomic reclassification effected by the Seventh Report of the International Committee on Taxonomy of Viruses in 2000), the beet necrotic yellow vein virus (BNYVV)(23, 24) which is transmitted to the root of the beet by the soilborne fungus *Polymixa betae* (25).

The disease affects significantly acreages of the area where the sugar beet plant is grown for industrial use in Europe, USA and Japan and is still in extension in several places in Western Europe (26, 27). As there exists no practical method to effectively control the spread of the virus at a large scale by chemical or physical means (28), neither in the plants nor in the soil, the main focus has been to identify natural sources of resistance within the sugar beet germplasm and to develop by breeding, varieties of sugar beet plants expressing the resistance genes. A variety of such tolerance genes to the virus has been identified and, some have been successfully used in the breeding of commercial sugar beet varieties (29, 30, 31).

Only the use of BNYVV-resistant or tolerant varieties will enable farmers to grow sugar beet plants in BNYVV-infected areas where sugar beet plant is an essential component of the crop rotation and contributes significantly to the grower's income.

A number of detailed studies have shown that a difference in susceptibility to the BNYVV-infection among sugar beet genotypes or varieties, generally reflect difference in the diffusion or translocation of the virus in the root tissues (32).

However, there are still few reports which indicate clearly that the tolerance genes, even from differing sources of sugar beet germplasm or wild relatives germplasm (33), would provide distinct mechanisms of resistance. Such a situation would represent a more manageable situation to design long lasting BNYVV-resistance strategies.

Since 1986, a number of reports and publications have described the use of isolated viral gene sequences expressed in plant to confer a high level of tolerance against the virus or even to confer a broad spectrum type of resistance against a number of related viruses (34, 35, 36). One of the most documented viral resistance strategy based on genetic engineering, in many cultivated species such as potato, squash, cucumber or tomato, is the use of the viral gene sequence encoding the coat-protein of the target virus (37) which under the control of plant regulatory elements, will be expressed in the plant.

However in the case of the coat-protein mediated resistance, the expression of a certain level of resistance in the transgenic plant might be attributed to different mechanisms such as RNA co-suppression and not necessarily to the production of the protein sequence.

In general, the virus sequence will be transformed in an appropriated cell or a tissue culture of the plant species using an Acrobacterium mediated transformation system or a direct gene transfer method according to the constraints of the tissue culture or cell culture method which can be successfully applied in a given species. A whole plant will be regenerated and the expression of the transgene will be characterized.

Though sugar beet is known as a recalcitrant species in cell culture, limiting the extent of practical genetic engineering applications in that species, there are number of isolated reports of successful transformation and regeneration of whole plants (38). A few examples of engineering tolerance to the BNYVV by transforming and expressing the BNYVV coat-protein sequence in the sugar beet genome have also been published (39, WO91/13159) though they rarely report data on whole functional transgenic sugar beet plants (40). In particular, reports show limited data on the level of resistance observed in infected conditions with transgenic sugar beet plants transformed with a gene encoding a BNYVV coat-protein sequence (41, 42).

A complete technology package including a sugar beet transformation method and the use of the expression of the BNYVV coat-protein sequence as resistance source in the transgenic sugar beet plant obtained by said transformation method has been described in the Patent Application WO91/13159.

Based on the information published, it can not be concluded that the coat-protein mediated resistance mechanism provides any potential for conferring to the sugar beet plant a total immunity to the BNYVV-infection by inhibiting completely the virus multiplication and diffusion mechanisms. To identify a resistance mechanism which enables to block significantly the spread of the virus at the early stage of the infection process would be a major criteria of success to develop such a transgenic resistance, in addition to the fact that even a level of resistance comparable to those known from the genes of resistance identified within the sugar beet germplasm would diversify the mechanisms of resistance available.

Because the disease is shown to expand in many countries or areas, at a speed depending upon the combination of numerous local environmental and agricultural factors, there is a major interest to diversify the sources of genetic resistance mechanisms which may, alone or in combination, confer a stable and long lasting resistance strategy in the current and future varieties of sugar beet plants which are grown for industrial use.

The publication of Xu H. et al. (Plant Cell Report, Vol. 15, pp. 91–96 (1995)) describes genetically engineering resistance construct to potato virus X in four commercial potato cultivars. However, said document states that transgenic potato clones which have included the 8KG gene (the TGB3 construct). However, when these transgenic plants were challenged with PVX, there was no protection against PVX suggesting that the OK protein does not play a role in the protection against PVX.

AIMS OF THE INVENTION

The present invention aims to provide a new method for introducing various viral resistances into a cell and a plant and the viral resistant cell and plant obtained.

A main aim of the invention is to provide a new method for introducing BNYVV resistance into a cell and a plant and the BNYVV-resistant cell and plant, in particular a sugar beet cell and plant (*Beta vulgaris* ssp.), obtained.

SUMMARY OF THE INVENTION

The present invention provides the use of an alternative sequence of plant virus, especially the BNYVV, to obtain a high degree of tolerance to the viral infection, in particular to ensure a rapid and total blocking of virus multiplication and diffusion mechanisms in a plant, especially in the sugar beet plant (*Beta vulgaris*), including fodder beet, Swiss Whard and table beet, which may also be subject to this viral infection. Expression of the resistance will be obtained in transgenic cell and plant, especially sugar beet cells and plants produced by the transformation method subject to the Patent Application WO95/10178 or by other transformation methods based on *Agrobacterium tumefaciens* or direct gene transfer. Because of its high efficiency, the transformation method as described in WO95/10178 enables the production of large numbers of transformated plants, especially sugar beet plants, and will be preferred to develop transgenic plants which may be analysed and characterized for their level of viral resistance, especially BNYVV Resistance, including their field evaluation.

The genome of beet necrotic yellow vein furovirus (BNYVV) consists of five plus-sense RNAs, two of which (RNAs 1 and 2) encode functions essential for infection of all plants while the other three (RNAs 3, 4 and 5) are implicated in vector-mediated infection of sugar beet (*Beta vulgaris*) roots (1). Cell-to-cell movement of BNYVV is governed by a set of three successive, slightly overlapping viral genes on RNA 2 known as the triple gene block (TGB)(2), which encode, in order, the viral proteins P42, P13 and P15 (gene products are designated by their calculated $M_r$ in kilodalton (3).

In the following description, the TGB genes and the corresponding proteins will be identified by the following terms: TGB1, TGB2, TGB3 or by their encoded viral protein number P42, P13 and P15. TGB counterparts are present in other furoviruses (4, 5), and in potex-, carla- and hordeiviruses (6).

In the table 1 are represented viruses having a TGB3 sequence, the molecular weight of TGB3 of said viruses, their host and references.

TABLE 1

| Virus | Size of TGB3 | Host | Reference |
|---|---|---|---|
| Apple stem pitting virus | 8 kDa | apple | Jelkman, J. Gen. Virol. 75, 1535–1542 (1994) |
| Blueberry scorch virus | 7 kDa | blueberry | Cavileer et al., J. Gen. Virol. 75, 711–720 (1994) |
| Potato virus M | 7 kDa | potato | Zavriev et al., J. Gen. Virol. 72, 9–14 (1991) |
| White clover mosaic virus | 8 kDa | clover | Forster et al., Nucl. Acids Res. 16, 291–303 (1988) |
| Cymbidium mosaic virus | 10 kDa | orchid | Neo et al., Plant Mol. Biol. 18, 1027–1029 (1992) |
| Barley stripe mosaic virus | 17 kDa | barley | Gustafson et al., Nucl. Acids Res. 14, 3895–3909 (1986) |
| Potato mop top virus | 21 kDa | potato | Scott et al., J. Gen. Virol. 75, 3561–3568 (1994) |
| Peanut clump virus | 17 kDa | peanut | Herzog et al., J. Gen. Virol. 75, 3147–3155 (1994) |
| Beet soil-borne virus | 22 kDa | sugar beet | Koenig et al., Virology 216, 202–207 (1996) |

The Inventors propose herewith a new method for providing resistance to plant viruses into a plant by blocking virus multiplication and diffusion mechanisms into said plant, especially into its root tissue. In order to demonstrate said resistance, the Inventors describe hereafter the effect of the overexpression of TGB sequences alone or in combination upon BNYVV multiplication and diffusion mechanism in plants of *C. quinoa* which are also the hosts of the BNYVV virus and which could be more easily manipulated by the man skilled in the art.

The Inventors have also made experiments upon *Beta macrocarpa*. These results have shown that it will be possible to obtain also the transformation of plants by the method according to the invention and obtain expression of TGB3 gene by said plants. Therefore, as explained in the following description, said method could be used to obtain various viral resistances into various plants species subject to infection by viruses characterized by the presence of a TGB3 sequence in their genome.

It is known that BNYVV does not require synthesis of viral coat protein for production of local lesions on leaves of hosts such as *Chenopodium quinoa* (7), indicating that virion formation is not required for cell-to-cell movement.

However, the manner in which the TGB components assist in the movement process is not understood although computer-assisted sequence comparisons have detected characteristic conserved sequences which may provide clues to their function. Thus, the 5'-proximal TGB protein (TGB1) invariably contains a series of sequence motifs characteristic of an ATP/GTP-binding helicase while the second protein (TGB2) always has two potentially membrane-spanning hydrophobic domains separated by a hydrophllic sequence which contains a highly conserved peptide motif of unknown significance (6). The sequence and size of the third TGB protein (TGB3) is more variable although the N-terminal portion is generally rather hydrophobic. Subgenomic RNAs with 5'-termini mapping upstream of the BNYVV TGB1 and TGB2 open reading frames (ORFs) have been detected (FIG. 1) but no such species has been reported for TGB3 of BNYVV (2), or of any other of the TGB-containing viruses. In the case of potato virus X (PVX; ref 8) and barley stripe mosaic virus (BSMV; ref. 9), there is evidence that the TGB2 and TGB3 products are expressed from the same subgenomic RNA.

So far, no example has been reported of a virus in which the three TGB members are arranged differently on the same RNA or are parcelled out to different genome RNAs, suggesting that their association in a particular order might be important in regulating their function.

The present invention concerns a method for inducing viral resistance to a virus comprising a triple gene block (TGB) with the proviso that it is not the potato virus X. Said virus is preferably selected from the group consisting of the apple stem pitting virus, the blueberry scorch virus, the potato virus M, the white clover mosaic virus, the *Cymbidium mosaic* virus; the barley stripe mosaic virus, the potato mop top virus, the peanut clump virus and the beet soil-borne virus; said method comprises the following steps:

- preparing a nucleic acid construct comprising a nucleic acid sequence corresponding to at Least 70% of the nucleic acid sequence of TGB3 of said virus or its corresponding cDNA, being operably linked to one or more regulatory sequence(s) active in a plant,
- transforming a plant cell with the nucleic acid construct, and possibly
- regenerating the transgenic plant from the transformed plant cell.

Preferably, the plant is a plant which may be infected by the above-described virus and is preferably selected from the group consisting of apple, blueberry, potato, clover, orchid, barley, peanut and sugar beet.

The present invention concerns also the obtained plant cell and transgenic (or transformed) plant (made of said plant cells) resistant to said viruses and comprising said nucleic acid construct.

The Inventors have also discovered unexpectedly that it is possible to induce BNYVV-resistance into a plant by a method which comprises the following steps:

preparing a nucleic acid construct comprising a nucleic acid sequence corresponding to at least 70%, preferably at least 90%, of the nucleic acid sequence of comprised between the nucleotides 3627 and 4025 of the 5' strand of the genomic or subgenomic RNA 2 of the BNYVV or its corresponding cDNA, being operably linked to one or more regulatory sequence(s) active in a plant, transforming a plant cell with said construct, and possibly regenerating a transgenic plant from the transformed plant cell.

The nucleic acid sequence comprised between the nucleotides 3627 and 4025 of the 5' strand of the genomic or subgenomic RNA 2 encoding the P15 protein is described in the FIG. 6 and in the publication (3). Said nucleic acid sequence and the corresponding amino acid sequence are described in the following specification as SEQ ID NOS: 1 and 2 respectively.

Another aspect of the present invention concerns a plant cell and a transgenic plant (made of said plant cells) resistant to BNYVV and comprising a nucleic acid construct having a nucleic acid sequence corresponding to at least 70%, preferably at least 90%, to the nucleic acid sequence comprised between the nucleotides 3627 and 4025 of the 5' strand of the genomic or subgenomic RNA 2 of BNYVV or the corresponding cDNA, being operably linked to one or more regulatory sequence(s) active in the plant.

Preferably, said plant cell or transgenic plant (made of said plant cells) resistant to BNYVV is obtained by the method according to the invention.

The variants of the nucleic acid sequence described as SEQ ID NO. 1 comprise insertion, substitution or deletion of nucleotides encoding the same or different amino acid(s). Therefore, the present invention concerns also said variants of the nucleic acid sequence SEQ ID NO. 1 which present more than 70% homology with said nucleic acid sequence and which are preferably able to hybridize to said nucleic acid sequence in stringent or non-stringent conditions.

Preferably, said sequences are also able to induce BNYVV resistance into a plant.

The terms “induce a viral resistance into a plant” mean inducing a possible reduction or a significative delay into the appearance of infection symptoms, virus multiplication or its diffusion mechanisms into the plant, especially in the root tissue.

The regulatory sequence(s) of said nucleic acid sequence are promoter sequence(s) and terminator sequence(s) active into a plant.

The nucleic acid construct may also include a selectable marker gene, which could be used to identify the transformed cell or plant and express the nucleic acid construct according to the invention.

Preferably, the cell is a stomatal cell and the plant is a sugar beet (*Beta vulgaris* ssp.) made of said cells.

According to the invention, the promoter sequence is a constitutive or foreigner vegetal promoter sequence, preferably selected from the group consisting of 35S Cauliflower Mosaic Virus promoter sequence, polyubiquitin Arabidopsis thaliana promoter (43), a promoter which is mainly active in root tissues such as the par promoter of the haemoglobin gene from Perosponia andersonii (Landsman et al. Mol. Gen. Genet. 214:68–73 (1988)) or a mixture thereof.

A last aspect of the present invention is related to a transgenic plant tissue such as fruit, stem, root, tuber, seed of the transgenic plant according to the invention or a reproducible structure (preferably selected from the group consisting of calluses, buds or embryos) obtained from the transgenic plant or the cell according to the invention.

The techniques of plant transformation, tissue culture and regeneration used in the method according to the invention are the ones well known by the person skilled it the art. Such techniques are preferably the ones described in the International Patent Applications WO95/10178 or WO91/13159 corresponding to the European Patent Application EP-B-0517833, which are incorporated herein by reference. These techniques are preferably used for the preparation of transgenic sugar beets according to the invention.

BRIEF DESCRIPTION OF THE DRAWINGS

FIG. 6 represents the nucleotides (SEQ ID NO: 1) and amino acid sequence of (SEQ ID NO: 2) TGB3 encoding the P15 of BNYVV.

DESCRIPTION OF THE INVENTION

Figure 1A:
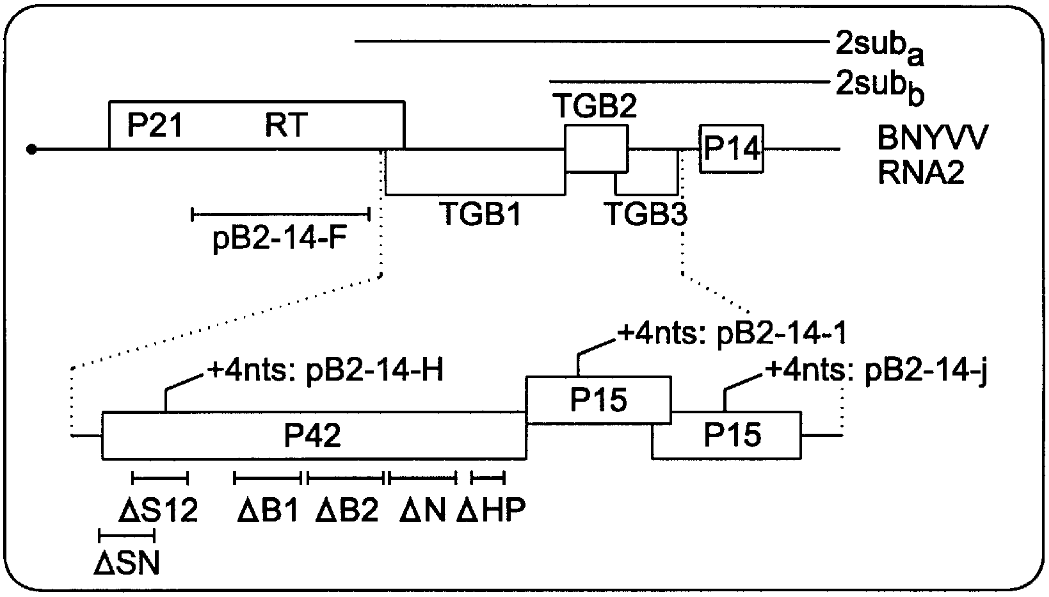
FIGS. 1(A–B) represents Structure of wild-type BNYVV RNA 2 and of replicons expressing TGB proteins.

In order to identify the potential use of particular gene sequences isolated from the viral RNA2 of BNYVV and to create BNYVV-resistance in a sugar beet via plant transformation, the Inventors have investigated whether independent expressions of the BNYVV TGB protein is possible by inserting the ORF of each into a viral replication-dependant “replicon” derived from BNYVV RNA3. The Inventors have showed that in mixed infections of *C. quinoa* leaves, the BNYVV TGB1 or TGB2 protein so expressed can complement BNYVV RNA 2 containing a mutation disabling the corresponding TGB protein. No complementation was observed with a replicon containing TGB3, however, unless the TGB3 ORF was positioned downstream of the ORF for TGB2 in the replicon. When co-inoculated with wild-type RNAs 1 and 2, the replicon expressing the TGB3 ORF of BNYVV inhibited infection. The data are consistent with a model for expression of the TGB proteins in which translation of P15 from a dicistronic subgenomic RNA regulates P15 expression levels in vivo. The Inventors have also identified that high expression of P15 could ensure a rapid and total blocking of virus multiplication and diffusion mechanisms in the plant.

MATERIALS AND METHODS cDNA clones

The transcription vector for production of wild-type full-length BNYVV RNA 1 and RNA 2 were pB15 (10) and pB2-14 (11), respectively. Transcription vectors for previously described RNA 2 mutants were pB2-14-F, -H, -I and -J (2) and pB2-14-ΔSN, -ΔS12, -ΔS37, -ΔB1, -ΔB2, -ΔB2, -ΔN and -GAA (11). The RNA 2 deletion mutant pB2-14-HP1 was produced by elimination of the sequence between nucleotides 3158 and 3258. The empty BNYVV RNA 3-derived replicon, rep0, was obtained by transcription of the RNA 3 deletion mutant pB35AΔES (12). TGB sequences for insertion into rep0 were amplified by the polymerase chain reaction (PCR) using primers which each contained a non-templated BamHI site at their 5'-extremity. PCR fragments corresponding to the P42 gene (nucleotides 2127–3297), the P13 gene (nucleotides 3282–3650), the P15 gene (nucleotides 3627–4025) and both the P13 and P15 genes (nucleotides 3282–4025) were digested with BamHI and inserted into BamHI-cleaved pB35AΔES. The resulting constructs were used to transcribe rep42, rep13, rep15, and rep1315, respectively. A replicon containing a frameshift mutation in the P15 ORF (Rep15-X) was produced by filling in the overhangs of an insert XbaI site (nucleotide 3948). The insert frameshift mutations in rep13-I, rep1315-I and rep15-J were created as described for the corresponding mutations in full-length RNA 2 (2). Cloned PCR-amplified sequences were verified to be error-free by sequencing (13).

In vitro transcripts

Capped transcripts were prepared by bacteriophage T7 polymerase run-off transcription (10) of plasmid DNA linearized by HindIII for pB15 and the replicon constructs and by SalI for pB2-14 and related constructs. Transcript concentration and integrity were evaluated by agarose gel electrophoresis. Leaves were mechanically inoculated with 50 $\mu$l per leaf of inoculation buffer containing 1 $\mu$g of each transcript (2). In some experiments, the RNA 1 and 2 transcripts were replaced by 0.025 $\mu$g of the highly infectious viral RNA purified from BNYVV isolate Stras 12 (10). Preliminary experiments showed that this amount of viral RNA was approximately equivalent in infectivity (as measured by a local lesion assay) to a mixture containing 1 $\mu$g each of the RNA 1 and 2 transcripts. For protoplast infections, 0.5 $\mu$g of viral RNAs 1 and 2 plus 3 $\mu$g replicon transcript were inoculated to $2.10^5$ protoplasts by electroporation (2).

Transcripts obtained from replicons were translated in a wheat germ extract (14) and the [$^{35}$S]-labelled translation products were visualized by autoradiography after SDS-PAGE (15, 16). Radioactivity incorporated into translation products was quantified with a Fujix MAS1000 BioAnalyzer and the values were adjusted for methionine content in calculating relative translation levels.

Detection of viral RNA and proteins

Total RNA was extracted (2) from inoculated leaves 10 days post-inoculation (pi) and from protoplasts 48 hr pi. Viral RNA was detected by northern hybridization with $^{32}$P-labelled antisense viral RNA transcripts (17) as probes. The RNA 1-specific probe was complementary to nucleotides 4740–5650, the RNA 2-specific probe to nucleotides 2324–3789 and the RNA 3-specific probe to nucleotides 1–380. P42, P14 and coat protein were detected by Western blot of total protein extracts of infected protoplasts using a rabbit polyclonal antiserum specific for each protein (18). The stability of mutations introduced into RNA 2 was tested by the polynucleotide chain reaction following reverse transcription (RT-PCR) of total RNA extracts from infected plants. Reverse transcripts were produced with an Expand™ reverse transcription kit (Boehringer) following the manufacturer's instructions. PCR was carried out essentially as described (19) using 25 cycles of the following regimen: 94° (30 sec), 50° (30 sec), 72° (3 min). Primer pairs for PCR amplification of different regions of the RNA 2 CDNA corresponded to (or were complementary to, in the case of the second member of each pair of primers) nucleotides 1143–1151 and 3393–3412 (P42 gene), and nucleotides 3151–3169 and 4128–4148 (P13 and P15 genes). The primer used to initiate cDNA synthesis prior to the PCR reactions was complementary to nucleotides 4128–4148.

RESULTS

Replicons expressing the BNYVV TGB proteins

Provided that sufficient sequences at the 3'- and 5'-extremities are retained, a BNYVV RNA 3 transcript from which the central region has been deleted can replicate efficiently on *C. quinoa* leaves when coinoculated with RNAs 1 and 2, and can express a foreign gene inserted in place of the deleted sequence (12, 20). The Inventors have used such an RNA 3-based "replicon" to express each of the BNYVV TGB proteins out of their normal context in RNA 2 and tested the capacity of each replicon to complement an RNA 2 mutant defective in the corresponding TGB gene.

Figure 1B:
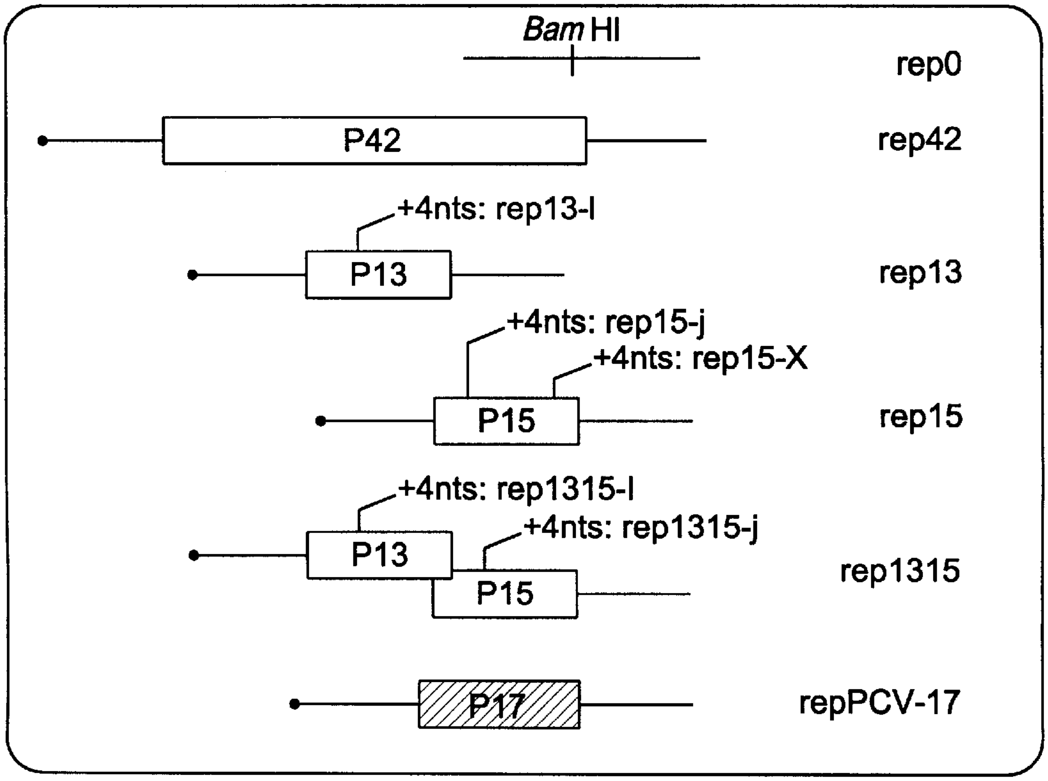
Figure 2A:
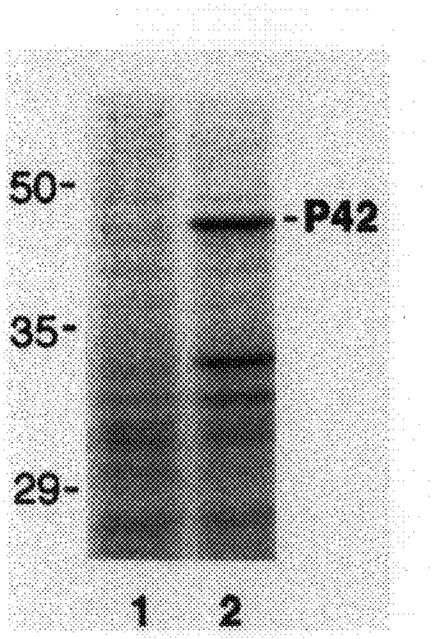
FIGS. 2(A–B) represents the In vitro translation of the replicons of the TGB genes in wheat germ extract.
Figure 2B:
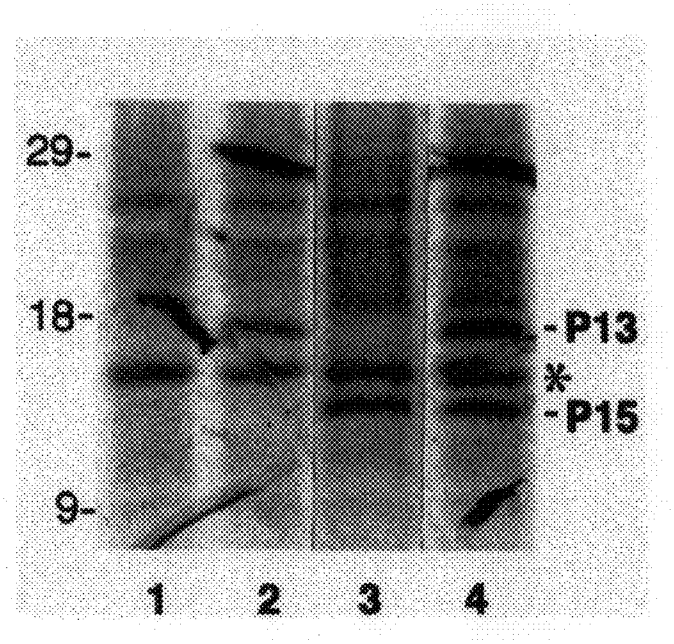

The replicons employed in this study are depicted in FIG. 1. FIG. 1A is the Genome map of RNA 2. The TGB genes are shaded and lines above the map indicate the extents of the subgenomic RNAs $2sub_a$ and $2sub_b$. The positions of deletions and frameshift-inducing insertions in RNA 2 are indicated. The 5'-terminal cap structure is denoted by a circle. P21 is the major viral coat protein. RT=readthrough domain (3). (B) BNYVV RNA 3-derived replicons containing the TGB genes of BNYVV (light shading) or the TGB3 gene encoding P17 of peanut clump virus (PCV) (dark shading). The BamHII site in the empty replicon (rep0) used for insertion of the PCR-amplified TGB sequences is shown. The positions of frameshift-inducing insertions in the various P13 and P15 mutant replicons are indicated. In addition to the constructs rep42, rep13 and rep15, which each contain a TGB gene, a fourth construct (rep1315) was produced containing both the P13 and P15 genes arranged in the same relative configuration as in RNA 2. The ability of each replicon to direct expression of the inserted gene or genes was tested by in vitro translation of the transcript in a wheat germ extract. The rep42, rep13 and rep15 transcripts each directed synthesis of an abundant product (FIG. 2A, lane 2; FIG. 2B, lanes 2 and 3), which was not produced in translations programmed with transcript corresponding to the empty replicon, rep0 (FIG. 2A, lane 1; FIG. 2B, lane 1). In the FIG. 2 (A), are represented $S^{35}$-methionine-labelled translation products of the empty replicon rep0 (lane 1) and rep42 (lane 2) displayed by autoradiography following PAGE (15). The indicated band was identified as P42 by comparison of its mobility to that of molecular weight markers (not shown). In the FIG. 2 (B), are represented translation products directed by rep0 (lane 1), rep13 (lane 2), rep15 (lane 3) and rep1315 (lane 4) displayed by autoradiography following PAGE (16). The bands tentatively identified as P13 and P15 are indicated to the right. The background band denoted by an asterisk was also synthesized when no transcript was introduced into the translation extract. The relative mobilities of the various translation products were as expected except that the putative P13 migrated slightly more slowly than P15, presumably because of its nontypical, amino acid composition. The dicistronic construct rep1315 directed synthesis of both P13 and P15 (FIG. 2B, lane 4) in relative molar amounts of 3:1

(values corrected for the difference in methionine contents of the two proteins; if the N-terminal methionine of each protein is removed post-translationally, the molar ratio is 5:1).

Figure 3A:
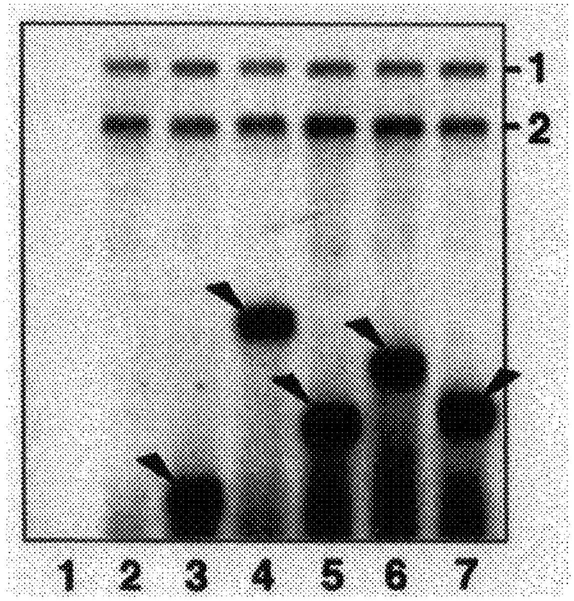
FIGS. 3(A–B) represents the amplification of the replicons encoding the TGB proteins in *Chenopodium quinoa* protoplasts and expression of P42.
Figure 3B:
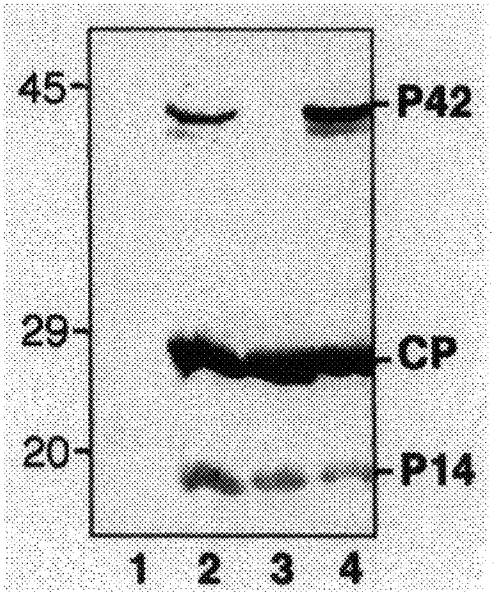

The capacity of the replicons to be amplified by the viral replication machinery in vivo was tested by coinoculating replicon transcripts to *C. quinoa* protoplasts along with BNYVV RNA's 1 and 2. Northern blot analysis of total RNA extracted from the protoplasts 48 hr pi revealed that all the replicons containing the TGB genes were efficiently amplified (FIG. 3A). The FIG. 3 (A) represents detection by northern hybridization of viral RNAs in *C. quinoa* protoplasts inoculated with BNYVV RNAs 1 and 2 alone (lane 2) or supplemented with rep0 (lane 3), rep42 (lane 4) rep13 (lane 5) rep1315 (lane 6) and rep15 (lane 7). RNA from mock-inoculated protoplasts was analyzed in lane 1. The protoplasts were harvested 48 hr pi and viral RNAs were detected using $^{32}$P-labelled viral RNA-specific antisense RNA probes. The replicons are indicated by arrow heads. The FIG. 3 (B) represents Immunodetection of P42 in total protein extracts of *C. quinoa* protoplasts inoculated with BNYVV RNAs 1 and 2 (lane 2), transcript of wild-type RNA 1 plus transcript of the RNA 2 mutant pB2-14-H, which contains a frameshift mutation in the P42 gene (11)(lane 3), the RNA 1 and pB2-14-H transcripts plus rep42 (lane 4). Protein extracted from mock-inoculated protoplasts was analyzed in lane 1. After PAGE (15) and electrotransfer to nitrocellulose, P42, major viral coat protein (CP) and P14 were immunodetected with a mixture of antisera specific for each protein (18). The positions of molecular weight standards are labelled in kilodaltons to the left of the blot. Western blot analysis revealed that the P42 level in protoplasts infected with a mixture of rep42 plus transcripts of RNA 1 and the frameshift mutant pB2-14-H, caused by filling in an SpeI site within the P42 gene of RNA 2 (see FIG. 1), was about twice that in protoplasts infected with RNA 1 plus wild-type RNA 2 (FIG. 3B, lanes 2 and 3). Note that the levels of accumulation of two other immunodetectable RNA 2 gene products (the major viral coat protein and P14; FIG. 1) were not modified by the presence of rep42. P13 and P15 could not be immuno-detected in such experiments.

The BNYVV TGB proteins can be complemented in trans

The ability of the replicons containing the TGB genes to supply movement functions in whole plants was tested by coinoculating leaves of the local lesion host *C. quinoa* with one of a series of RNA 2 transcripts containing a mutation disabling a TGB gene plus a replicon containing the corresponding wild-type gene. In all experiments, the inoculum also contained transcript of wild-type RNA 1 as source of viral RNA-dependent RNA replicase, although this fact will not always be stated explicitly below. For the P42 gene, the RNA 2 mutants tested included the frameshift mutant (pB2-14-H) caused by filling in an SpeI site at nucleotide 2280, a series of mutants containing short inframe deletions at different positions in the P42 ORF (mutants pB2-14-ΔS12, -ΔSN, -ΔB1, -ΔB2, -ΔN, and -ΔHP1; FIG. 1A; also see ref. 11), and a deletion mutant (pB2-14-F; FIG. 1) where removal of a 935 nucleotide sequence upstream of the P42 ORF has inactivated the promoter for the subgenomic RNA (RNA 2sub$_a$) responsible for P42 synthesis. Inocula containing RNA 1 transcript plus any one of the above mutant RNA 2 transcripts did not produce local lesions on *C. quinoa* and no progeny viral RNA could be detected in the inoculated leaves 10 days pi (FIG. 4, lanes 3 and 5; see ref. 11 for the other mutants). In the FIG. 4, the replicon indicated at the top of each lane was inoculated to leaves of *C. quinoa* together with wild-type RNA 1 transcript plus either wild-type RNA 2 transcript (lane 2) or the mutant RNA 2 transcript identified above each lane. In lanes 19 and 20 the inoculum contained rep42 and rep15 (lane 19) or rep42 and rep1315 (lane 20), in addition to RNA 1 and pB2-14- HP1 transcripts. Lane 1 contains RNA from a non-inoculated control plant. Inoculated leaves were harvested 10 days pi and tested for viral RNA contents by northern hybridization as described in FIG. 3. The positions of replicons are indicated by arrows. When rep42 transcript was included in the inoculum, numerous local lesions (20–80 per leaf) appeared on the inoculated leaves except for the inoculum containing transcript of the RNA 2 deletion mutant pB2–14-HP1, which remained symptomless . The resulting pale green lesions were similar in appearance to those elicited by inoculation with RNA 1 plus wild-type RNA 2 except for the RNA 2 mutant pB2-14-F, where necrotic local lesions were formed. In this later case, the necrotic lesion phenotype may be related to production of a truncated form of the readthrough (RT) protein by this RNA 2 mutant (7).

Figure 4:
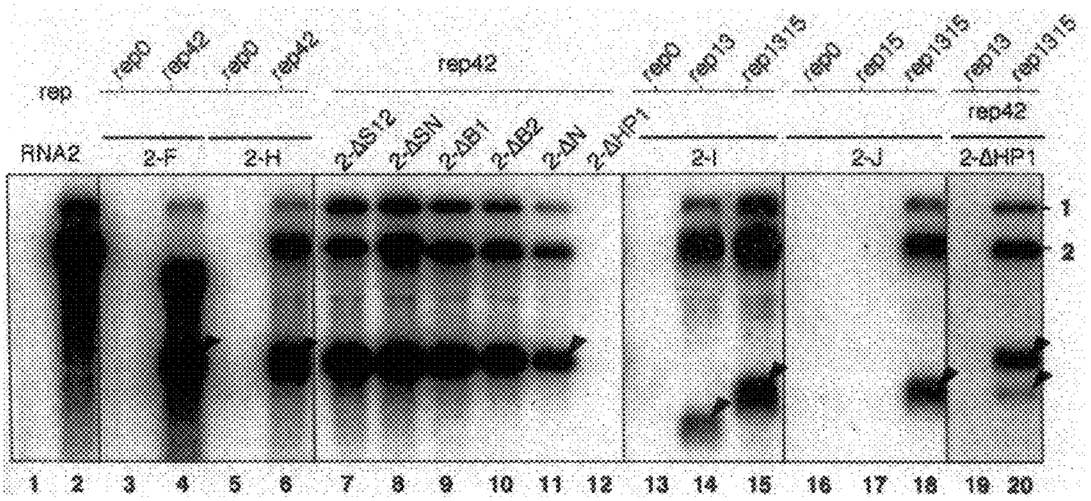
FIG. 4 represents the complementation of RNA 2 transcripts containing defects in the different TGB genes by the corresponding wild-type gene supplied from a replicon.

Northern hybridization of the inoculated leaves 10 days pi revealed the presence of progeny viral RNAs of the length expected for RNAs 1, 2 and rep42 for all the RNA 2 mutants (FIG. 4, lanes 2, 4, 7–11) except the deletion mutant pB2-14-HP1 (FIG. 4, lane 13). As will be shown below, the failure of pB2-14-ΔHP1 to be complemented by rep42 is probably due to deletion of the promoter for the subgenomic RNA (RNA 2sub$_b$), which is believed to direct translation of the downstream TGB proteins.

Similar complementation experiments were carried out with rep13, rep15 and the dicistronic construct rep1315. Both rep13 and rep1315 were able to complement accumulation on leaves (FIG. 4, lanes 14 and 15) of the mutant pB2-14-I, in which the P13 gene had been disabled by insertion of four nucleotides (the insertion created an XhoI site), although the resulting local lesions were necrotic. Necrotic local lesions were also produced during mixed infections with the aforesaid replicons and wild-type RNA 1 and 2 (see below), indicating that the replicon-related symptom phenotype is dominant over the wild-type. The novel symptoms may be related to differences in the time course of synthesis or the level of accumulation of P13 when it is expressed from the replicon rather than full-length RNA 2.

In experiments such as those described above, it is important to demonstrate that the mutation originally introduced into the P42 or P13 gene on the RNA 2 transcript was still present in the progeny RNA 2, that is, the defective copy of the TGB gene on the transcript had not been converted to the wild-type by RNA recombination in planta (21) with the copy present on the replicon. Therefore, an RT-PCR experiment was carried out on the progeny viral RNA from a plant infected with RNA 1, pB2-14-H transcript (P42 gene disrupted by filling in an SpeI site) and rep42. The primer pair used in the RT-PCR hybridized to RNA 2 sequences flanking the P42 gene and hence amplifies the copy cf the gene present in RNA 2 but not the copy on the replicon, where the flanking sequences are absent. Restriction enzyme analysis revealed that the SpeI site was absent in the resulting amplified DNA fragment, as expected for the mutated rather than the wild-type form of the TGB gene. Similar analysis of progeny viral RNA from plants infected with RNA 1, pB2-14-I (frameshift mutation in P13 gene creating anXhoI site) and either rep13 or rep1315 similarly demonstrated that the mutation disabling the copy of the P13 gene on the RNA 2 transcript was conserved in the progeny RNA 2. We conclude that rep42 and rep13 are indeed complementing P42 and P13 function by supplying the gene product in trans rather than simply serving as a source of the wild-type TGB sequence for recombination.

Unexpectedly, the replicon expressing the wild-type P15 gene (rep15) was unable to complement the P15-defective RNA 2 mutant pB2-14-J in mixed inoculations. No local lesions formed on the inoculated leaves 10 days pi and no viral RNA could be detected in the leaves by northern blot (FIG. 4, lane 17). On the other hand, when pB2-14-J transcript was coinoculated with rep1315, local lesions (of the necrotic type) appeared and progeny viral RNAs were readily detected (FIG. 4, lane 18). In this latter case, analysis of an RT-PCR product containing the P15 gene in the progeny RNA 2 revealed that the mutation disabling the gene was still present. Complementation of pB2-14-J still occurred when the P13 ORF in the dicistronic replicon was interrupted by a frameshift mutation (rep1315-I; FIG. 1), establishing that expression of full-length P13 from the first ORF of the dicistronic replicon is not required for complementation by the downstream copy of the P15 gene.

Evidence that P15 is expressed from a dicistronic subgenomic RNA

An RNA 2-derived subgenomic RNA (RNA $^2sub_b$) of about 1500 nucleotides length has been detected in BNYVV-infected tissue (2). The γ'-extremity of this species has not been mapped precisely but is predicted to lie near the 5'-terminus of the P13 ORF. No subgenomic RNA with 5'-end upstream of the P15 ORF has been detected, raising the possibility that, as in BSMV (8), P13 and P15 are both expressed from RNA 2subb.

The aforementioned inability of rep42 to complement the P42-defective RNA 2 mutant pB2-14-HP1 could stem from polar effects of the RNA 2 deletion on synthesis of downstream TGB proteins if the deletion has disabled the RNA $2sub_b$ promoter (The right-hand boundary of the deletion in pB2-14-ΔHP1 is only 30 residues upstream of the P13 initiation codon). To test this hypothesis, an experiment was carried out in which the pB2-14-ΔHP1 transcript was complemented with both rep42 and rep1315. Leaves inoculated with this mixture developed local lesions and contained progeny viral RNA's (FIG. 4, lane 20). If, on the other hand, rep13 rather than rep1315 was used along with rep42 to complement pB2-24-HP1, no symptoms appeared and no progeny viral RNA's were detected by northern blot (FIG. 4, lane 19). These observations are consistent with the hypothesis that the pB2-14-HP1 deletion interferes with expression of the downstream TGB ORF's, presumably by blocking RNA $2sub_b$ transcription. Furthermore, the fact that complementation was successful with rep1315 but not with rep13 indicates that P15 as well as P13 is translated from RNA $2sub_b$.

Independent expression of P15 inhibits infection with wild-type viral RNA

The ability of rep1315 but not rep15 to complement the P15-defective RNA 2 mutant pB2-14-J in leaf infections could indicate that independent expression of P15 from the monocistronic replicon interferes with the viral infection cycle by producing the gene product in excessive quantities relative to P13. To test this hypothesis, an experiment was carried out in which rep15 was inoculated to *C. Quinoa* leaves along with wild-type viral RNAs 1 and 2. No lesions appeared on the inoculated leaves, even at late times pi (FIG. 5A), and no viral RNA could be detected by northern blot (FIG. 5B, lane 6). The FIG. 5 (A) represents leaves of *C. quinoa* inoculated with RNAs 1 and 2 (left) or RNAs 1 and 2 plus rep15 (right). The leaves were photographed 20 days pi when the local lesions on the leaf to the left had expanded so as to cover much of the leaf surface. In the FIG. 5 (B), analysis by northern hybridization (as described in FIG. 3) of the viral RNA contents of *C. quinoa* leaves inoculated with BNYVV RNAs 1 and 2 alone (lane 1) or together with rep0 (lane 2), rep42 (lane 3), rep13 (lane 4), rep1315 (lane 5), rep15 (lane 6), rep15-J (lane 7), rep15-X (lane 8) or repPCV-P17 (lane 9). The positions of replicons are indicated by arrows. (C) Analysis by northern hybridization of the viral RNA contents of the inoculated leaves (lanes 1, 3 and 5) and the roots (lanes 2, 4 and 6) of *Beta macrocarpa* either mock-inoculated (lanes 1 and 2), inoculated with 3NYVV RNAs 1, 2 and 3 (lanes 3 and 4) or with RNAs 1, 2 and 3 plus rep15 (lanes 5 and 6). RNA 3 was included in the inoculum because it is necessary for systemic movement in *B. macrocarpa* (22'. Under these conditions, leaves inoculated with RNAs 1 and 2 alone were heavily infected (FIG. 5A; FIG. 5B, lane 2). The inhibition of virus infection by rep15 was dose-dependent. Addition of ten times less rep15 to the inoculum mix still resulted in almost complete inhibition of lesion formation but lesser amounts of the replicon were progressively less effective in blocking the infection. Rep15 also blocked the appearance of progeny viral RNA in the inoculated leaves and in the roots of *Beta macrocarpa*, a systemic host of BNYVV (FIG. 5C, lanes 5 and 6). The empty replicon, rep0, and replicons expressing the other two TGB proteins (rep42, rep13, rep1315), on the other hand, did not significantly inhibit BNYVV infection of *C. quinoa* leaves (FIG. 5B, lanes 2–5).

Since rep15 did not interfere with amplification of RNA 1 and 2 in *C. quinoa* protoplasts (see FIG. 3), this suggests that the replicon interferes with movement of the virus from the initial site of infection into neighbouring cells (cell-to-cell movement) during local lesion formation on leaves. Lesion formation was not inhibited by coinoculation of Stras 12 RNA with the replicons rep15-J or rep15-X (FIG. 5B, lanes 7 and 8), which encode frameshift-truncated forms of P15. This finding confirms that expression of P15 from the replicon, rather than the simple presence of the corresponding RNA sequence, is required for inhibition during the mixed infection experiments. In the presence of rep15-X, however, the resulting local lesions were about one third the diameter of the lesions formed by infection with Stras 12 alone or with Stras 12 plus rep15-J and the content of progeny viral RNA in the infected leaves was significantly lower (FIG. 5B, lane 8). This finding suggests that the almost full-length P15 molecule produced by rep15-X, although incapable of substituting for wild-type P15 in a complementation experiment, can interfere with the cell-to-cell movement activity of the wild-type P15 produced from RNA 2. Presumably, the full-length and truncated forms of P15 compete with one another for binding sites on another component (which could be of either viral or cellular origin) involved in the movement process.

Figure 5A:
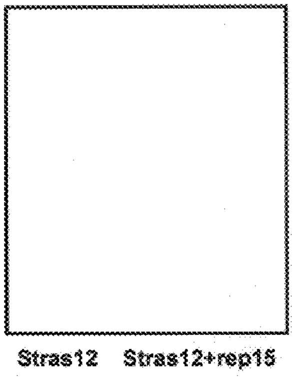
FIGS. 5(A–C) shows the effect of replicons on infection with wild-type BNYVV RNAs 1 and 2.
Figure 5B:
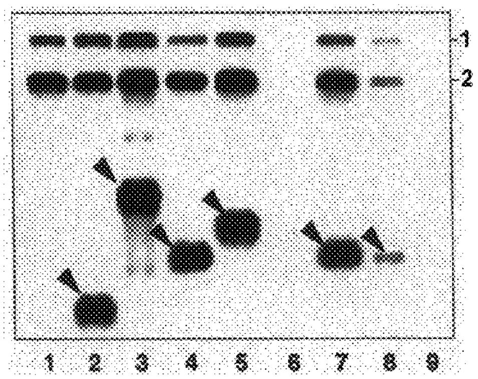
Figure 5C:
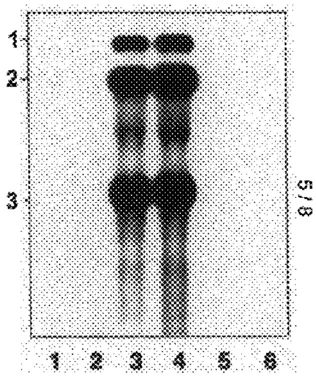

As noted above, sequence comparisons between different viruses possessing a TGB have revealed little sequence similarity between the different TGB3 genes. For example, the 17 kDa TGB3 protein (P17) of peanut clump furovirus (PCV) displays no significant sequence similarity with P15 of BNYVV (4) even though both viruses can infect *C. quinoa*. To determine whether independent expression of the PCV TGB3 protein can interfere with a BNYVV infection in a manner similar to that observed with rep15, a BNYVV RNA 3-derived replicon containing the PCV TGB3 (repPCV-P17;

FIG. 1) was constructed. *C. quinoa* leaves inoculated with BNYVV RNAs 1 and 2 plus repPCV-P17 did not develop symptoms and no progeny BNYVV RNA's could be detected by northern blot (FIG. 5A, lane 9). This observation suggests that the pathways by which BNYVV and PCV move from cell-to-cell in *C. quinoa* share at least one common element which, in spite of their dissimilarity in sequence, interacts with the TGB3 products of both viruses.

The Inventors have shown that replicons carrying P42 and P13 can complement BNYVV RNA 2 carrying the corresponding defective gene but that a replicon carrying P15 cannot. In the latter case, complementation can occur, however, if the P15 gene is supplied as the second gene on a dicistronic RNA (rep1315) carrying the P13 gene in first position. It should be noted that the relative disposition of the P13 and P15 genes on rep1315 is identical to their disposition on RNA 2$sub_b$, the subgenomic RNA which is believed to direct synthesis of both proteins in wild-type infections. This suggests that successful cell-to-cell movement of BNYVV requires the presence of P13 and P15 in appropriate relative amounts and that production of both proteins from the same subgenomic RNA represents a mechanism for coordinating their synthesis. The inability of rep15 to complement the P15 mutant RNA 2 transcript pB2-14-J and its ability to inhibit infection by wild-type virus would then both be due to over-production of P15 relative to P13 when the former is translated from the replicon and the latter from RNA 2. When P15 is expressed from the dicistronic replicon rep1315, on the other hand, appropriate relative P13–P15 levels would be produced, allowing cell-to-cell movement to proceed. The "correct" relative levels of accumulation of P13 and P15 in a wild-type infection are not known. Translation of rep1315 in wheat germ extract produced three to five times more P13 than P15 but such experiments do not necessarily reflect the situation in planta since the turnover rates of the two proteins may differ significantly. Note that these results indicate that TGB-mediated cell-to-cell movement is less sensitive to over-expression of P42 and P13 relative to the "correct" levels characteristic of a normal infection since co-inoculation of rep42, rep13 or rep1315 with wild-type virus did not inhibit infection (FIG. 5, lanes 3–5), although the lesions produced in the presence of rep13 and rep1315 were necrotic. Thus, it shows that expression of P15 in transgenic plants could provide a mechanism for inducing BNYVV-resistance ("pathogen-derived resistance"; ref. 23) in such plants, provided that sufficient P15 expression levels can be attained.

To gain a better understanding of how the relative levels of P13 and P15 are regulated during translation will require learning how the P15 cistron is accessed by ribosomes on RNA 2$sub_b$. Translation initiation at an internal cistron of a eucaryotic messenger RNA may occur by several mechanisms, including (i) leaky scanning, where a fraction of the ribosomal subunits which begin scanning the RNA at the 5'-end move past the first (non-optimal) upstream AUG without initiating (24), and (ii) internal entry, where ribosomal subunits bind directly to a special sequence on the RNA near the internal initiation codon (25). A third possible mechanism, termination-reinitiation (24), appears unlikely to apply to any of the TGB-containing viruses because the overlap between the TGB2 and TGB3 cistrons would require ribosomes to scan backwards after terminating TGB2 to reach the TGB3 initiation codon. It has been suggested that the TGB3 proteins of BSMV and PVX are translated by a leaky scanning mechanism (8, 9). The BNYVV P15 gene may also be produced by leaky scanning although it should be noted, however, that the context of the BNYVV P13 initiation codon (AUAAUGU) is nearly optimal and there are also two downstream AUG's which scanning subunits would have to ignore to reach the P15 initiation codon.

EXAMPLES

The following examples are transformation of plant made by the technique described in the International Patent Application WO95/10178 incorporated herein by reference.

The plant material and growth conditions were the ones described by Hall et al., Plant Cell Reports 12, pp. 339–342 (1993) Pedersen et al., Plant Science 95, pp. 89–97 (1993), and Hall et al, Nature biotechnology 14, 1996, in press.

Plasmid vectors and DNA preparation

The plasmid pET-P15 (harbouring the P15 nucleic acid sequence) was restricted at its single BamHI site and blunt-ended with T4 DNA polymerase. After purification by electrophoresis in 0.8% agarose gel, the linear plasmid was restricted at its single NcoI site. The P15 gene fragment of 400 bp was purified by electrophoresis and inserted into pMJBX-Ub (harbouring the Arabidopsis polyubiquitin promoter (Norris et al., Plant Molecular Biology 21, pp. 895–906 (1993), a TMV enhancer sequence and the Nos 3' terminator) cut with NcoI and SmaI restriction endonucleases. In the plasmid so obtained (pMJBX-Ub-P15), the nucleic acid sequence of the P15 gene is placed under the control of the Arabidopsis polyubiquitin promoter followed by the TMV enhancer sequence. The EcoRI fragment from plasmid pB235SAck contains the pat gene, used as the selective marker, encoding phosphinothricin acetyl transferase (obtained from Agrevo, Berlin Germany). On this EcoRI fragment, the nucleic acid sequence of the pat gene is under the control of the 5' and 3' expression signals of the Cauliflower virus. The plasmid pMJBS6, resulting from the combination of this EcoRI-pat fragment and a partial EcoRI digestion of plasmid pMJBX-Ub-P15, contains both the pat and the P15 genes. This pMJBS6 plasmid is a high-copy plasmid based on the pUC18 vector and contains also the -lactamase gene (amp$^r$). In the plasmid pIGPD7, harbouring the same pat fragment as pB235SAck, the -lactamase gene was replaced by an igpd (imidazole glycerol phosphate dehydratase) gene from Saccharomyces cerevisiae (Struhl et al., Proceedings of the National Academy of Science USA 73, pp. 1471–1475 (1976). Selection for and maintenance of the plasmid in *Escherichia coli* was achieved by complementation of an auxotrophic hisB strain SB3930 on minimal medium in the absence of antibiotics. The P15 fragment, with its ubiquitin promoter and terminator sequence, was purified as a 2500 bp fragment obtained from the pMJBX-Ub-P15 plasmid after it was cut at the single HindIII site, followed by a partial EcoRI restriction. This fragment was blunt-ended and inserted in a blunt-ended pIGPD7 plasmid, cut at the single NcoI site. The resulting pIGPDS4 plasmid contains both the pat and the P15 genes on a vector without the β-lactamase gene.

Plant material

In vitro shoot cultures of sugar beet plantlets were initiated to provide a reusable and uniform source of sterile starting material and were maintained with a 4-weekly subculture period as described by Hall et al., Plant Cell Reports 12, pp. 339–342 (1993).

Large-scale isolation of sugar beet epidermis

A modified version of the blender method by Kruse et al., Plant Physiology 690, pp. 1382–1386 (1989) was used. For each isolation, 2 g leaves (with the midribs removed) from 4 week old shoots was blended in a Waring blender at maximum speed (23000 rpm) for 60 sec in a 250 ml metal beaker containing 50 ml cold (4° C.) Ficoll medium (100 g/l Ficoll, 735 mg/l $CaCl_2.2H_2O$, 1 g/l PVP40, autoclaved). The epidermal fragments were then recovered on a 297 $\mu$m nylon filter and washed with 500 ml sterile tap water. These were rinsed from the filter into a 9 cm Petri dish using 10 ml CPW9M containing 3.8% (w/v) $CaCl_2.2H_2O$ (Krens et al., Theoretical and Applied Genetics 79, pp. 390–396 (1990). Any remaining leaf fragments were removed and dishes were preincubated for 1 h at room temperature.

Guard cell protoplast isolation from enriched epidermis fractions

To recover the epidermis fraction, the suspension was centrifuged for 1 min at 55×g after which the supernatant was removed. The pellet was resuspended in 50 ml enzyme mix and 5 ml aliquots were transferred to each of 10, 6 cm Petri dishes (Greiner, TC quality), sealed with parafilm and incubated overnight at 25° C. in darkness with gentle agitation. The digestion medium consisted of CPW9M supplemented with 0.5% (w/v) Cellulase RS and 3% (w/v) Macerozyme R10 (Yakult Honsha, Tokyo, Japan), pH 5.8. The following morning, the protoplasts were generally seen floating near the surface of the digestion mix. After gentle agitation of the suspensions using a sterile pipette to release the protoplasts still adhering to cuticle fragments, the digestions were pooled and passed through 297 and 55 μm nylon filters. The filtrate was mixed with an equal volume of iso-osmotic Percoll containing 15% (w/v) sucrose (Percoll15S) and divided over 12×12 ml centrifuge tubes. In each tube, first 1 ml CPW15S (Krens et al., 1990) and then 0.5 ml 9% (w/v) mannitol containing 1 mM $CaCl_2$ (9M) were carefully layered on top of the protoplast suspension. After centrifugation at 55×g for 10 min the viable guard cells were visible in bands at the CPW15S/9M interface. To concentrate the protoplasts, these bands were collected and mixed with Percoll15S to give a final volume of 16 ml. This was then divided between 2 centrifuge tubes, layered as above and recentrifuged. Careful removal of the 9M layers yielded the enriched guard cell protoplast fraction for subsequent counting using a haemocytometer.

Protoplast transformation

Transformations were performed in 12 ml centrifuge tubes, each containing $1\times10^6$ protoplasts suspended in 0.75 ml 9M medium. Plasmid DNA (50 μg of pMJBX-Ub-P15 and pIGPDS4) was added and, immediately after mixing, 0.75 ml PEG medium was added dropwise (40% PEG 6000 dissolved in F medium (Krens et al., Nature 296, pp. 72–74, (1982). After thorough mixing, the suspension was kept at room temperature for 30 min with intermittent agitation. Subsequently, at 5 min intervals, 4×2 ml aliquots of F medium were added. After centrifugation for 5 min at 55×g the supernatant was discarded and the protoplast pellet resuspended in 9M and recentrifuged. The cells were finally resuspended in 1 ml of 9M medium for counting.

Protoplast culture and selection

Protoplasts were embedded in Ca alginate and cultured in modified, liquid K8P medium (Hall et al., 1990). To select for stably transformed cells, bialaphos, the active compound of Herbiace (Meiji Seika Ltd, Japan) as added after 7 days, to give a final concentration of 200 μg/l. On day 18, the alginate discs were cut into 3 mm slices and transferred to PGo medium (De Greef and Jacobs, Plant Science Letters 17, pp. 55–61, 1979) supplemented with 1 μM BAP (PG1B) and 250 μg/l bialaphos and solidified with 0.8% agarose.

Callus culture and regeneration

After 21 days, the pieces of alginate containing the non-visible microcalli were transferred to 9 cm Petri dishes containing 20 ml Medium K (3% sucrose, 0.8% agarose, 1 μM BAP, PGo medium, pH=5.8 autoclaved). Culture was in the dark as above.

Friable, watery-type calli on reaching the size of approximately 1–2 mm in diameter, were individually picked off and cultured in groups of 20 on fresh Medium K. At this stage, PCR analyses confirmed the presence of transformants.

At two-weekly intervals all calli were subcultured on to fresh medium.

Regenerants appeared during the first 8 weeks of culture of individual calli. When the first shoots were visible and had reached a size of approximately 2 mm, the dish was transferred into the light (3000 lux), 25° C., 15 hour day length.

Plantlets approximately 4 mm long were transferred to individual culture tubes containing 15 ml of Medium K and were further subcultured in the light as above.

Rooting and transfer to the soil

When the plantlets had reached the four-leaf stages (usually after 5 to 6 weeks with one subculture after 3 weeks), they were transferred to culture tubes containing 15 ml of Medium L (3% sucrose, 0.8% agarose, 25 μM indolebutyric acid (IBA), PGO medium, pH=5.8 autoclaved)(PGo medium described by De Greef W. et al., Plants Science Letters 17, pp. 55–61 (1979)) and further cultured as above.

When at least one root had reached a length of 1 cm, the plantlets were removed from the culture tubes and washed under running tap water to remove all fragments of the agar, and transferred to soil in 9 cm pots in the greenhouse.

Plantlets were covered with a transparent plastic cup to provide a humid environment for 7 days, after which they could be grown without protection.

The plant transformed by the sequence SEQ ID NO. 1 according to the invention is recovered and has been expressed P15.

DNA analysis

Genomic DNA isolated from the primary transformants is electrophoresed in a 0.8% agarose gel after treatment with restriction enzymes and transferred to a nitrocellulose membrane using standard procedures, according to the manufacterer's protocol. Hybridisation is performed with the DNA, as $\alpha^{32}$P-dATP-labelled probes, whose presence it is desired to establish. The membranes were washed to a final stringency of 0.1%×SSC, 0.1% SDS at 60° C. The hybridized DNA is visualised by darkening the X-ray film for 24 to 48 hours.

PCR analysis

Standard PCR techniques were used to detect a range of intact plasmid sequences. Reactions were performed using 25 cycles of 1 min denaturation at 94° C., 1 min annealing; 2 min extension at 72° C., with a final extension period of 5 min. The annealing temperatures were optimized for each primer combination. The presence of the coding region of the BNYVV P15 gene in the sugarbeet genome was verified by PCR using a pair of oligonucleotides as primers: MOV1, sense primer SEQ ID NO: 3 [5'-GGTGCTTGTGGTTAAAGTAGATTTATC-3' (nucleotides 3 to 29 on SEQ ID NO 1)] and MOV2 antisense primer [5-CTATGATACCAAAACCAAACTATAGAC-3' (complementary to the nucleotides 369 to 395 on SEQ ID NO 1)]. This 393 bp long fragment comprises the whole coding region of the P15 gene for BNYVV (see FIG. 7).

Figure 7:
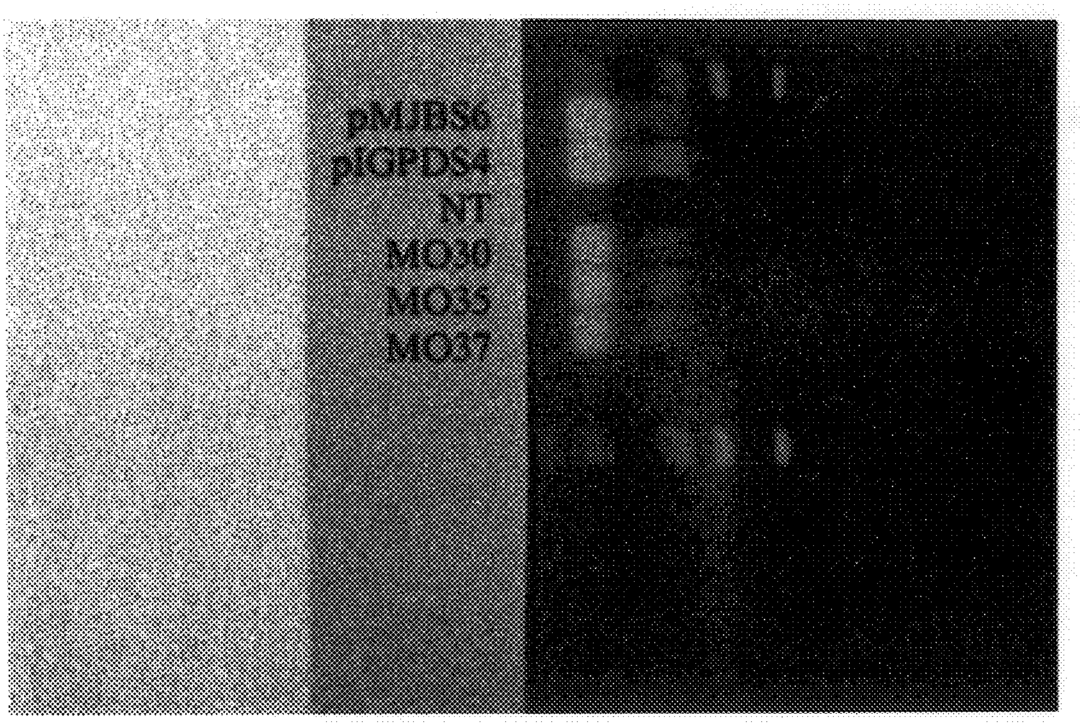
FIG. 7 shows the presence of the coding regions of the BNYVV p15 gene in the sugar beet genome by a PCR.

FIG. 7: Analysis of PCR products obtained with sugarbeet DNA from P15-transformants (lane 5 to 7) and an untransformed plant (lane 4). Low DNA Mass Ladder® (Life Technologies) was used as a size marker (lane 1). Lane 2 and 3 correspond to the positive controls (pMJBS6/pIGPDS4). The arrow on the left shows the position of the expected PCR product.

Southern blot hybridisation analysis

The integration of the BNYVV P15 gene in the sugarbeet genome was verified by Southern blot hybridisation. Total DNA of primary transgenic regenerants was isolated, digested with restriction enzymes (PstI, KpnI, NcoI, SacI), electrophoresed, blotted and hybridised with BNYVV P15-specific $^{32}P$-labelled probes using PCR amplified MOV1–MOV2 fragment (see FIG. 8).

Figure 8:
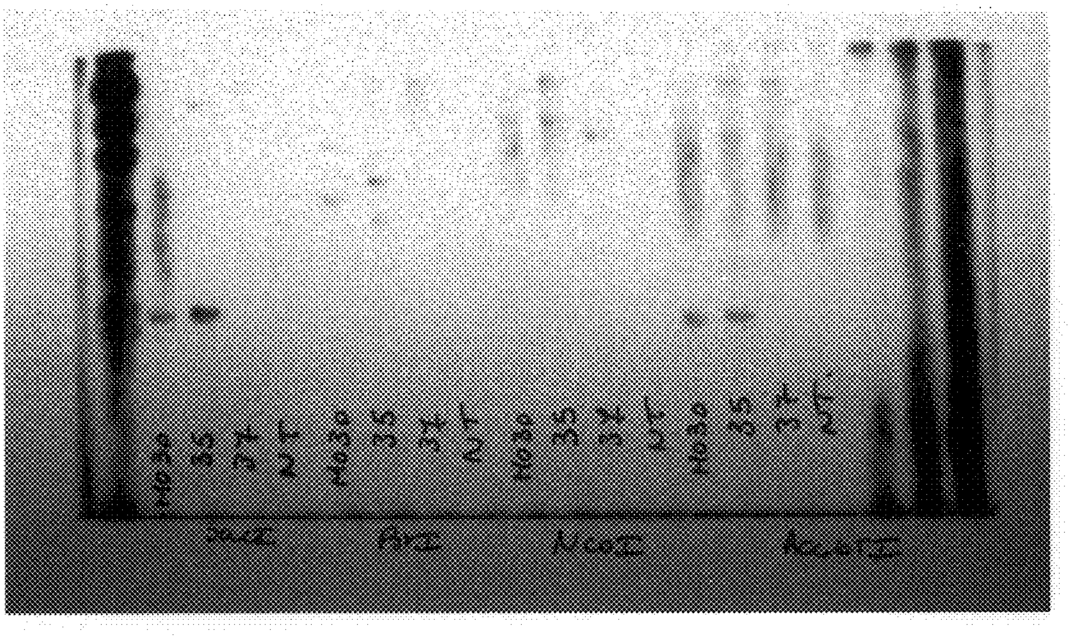
FIG. 8 shows the integration of the BNYVV P15 gene in the sugar beet genome by Southern blot hybridisation.

FIG. 8: Southern blot analysis. Lambda DNA digested with HindIII was used as a size marker (lane 1). Lanes 2 to 16, DNA of the transgenics: 2 to 4 digested with SaCI, 6 to 8 digested with PstI, 10 to 12 digested with NcoI, 14 to 16 digested with KpnI. Lanes 5, 9, 13 and 17 correspond to the untransformed plant.

REFERENCES

1. Richards K. E. & Tamada T., *Annu. Rev. Phytopathol.* 30, pp. 291–313 (1992)
2. Gilmer D. et al., *Virology* 189, pp. 40–47 (1992)
3. Bouzoubaa S. et al., *J. Gen. Virol.* 68, pp. 615–626 (1987)
4. Herzog E. et al., *J. Gen. Virol.* 18, pp. 3147–3155 (1994)
5. Scott K. P. et al., *J. Gen. Virol.* 75, pp. 3561–3568 (1994)
6. Koonin E. V . & Dolja V. V., *Crit. Rev. Biochem.* and *Mol. Biol.* 28, pp. 375–430 (1993)
7. Schmitt C. et al., *Proc. Natl. Acad. Sci. USA*. 89, pp. 5715–5719 (1992)
8. Morozov S. Y. et al., *J. Gen. Virol.* 72, pp. 2039–2042 (1991)
9. Zhou H. & Jackson A. C., *Virology* 216, pp. 367–379 (1996)
10. Quillet L. et al., *Virology* 172, pp. 293–301 (1989)
11. Bleykasten et al., *J. Gen. Virol.* 77, pp. 889–897 (1996)
12. Jupin I. et al., *Virology* 178, pp. 273–280 (1990)
13. Sanger F. et al., *Proc. Natl. Acad. Sci. USA* 74, pp. 5463–5467 (1977)
14. Fritsch C. et al., *J. Gen. Virol.* 46, pp. 381–389 (1980)
15. Laemmli U. K., *Nature* 227, pp. 680–685 (1972)
16. Schägger H. & von Jagow G., *Anal. Biochem.* 166, pp. 368–379 (1987)
17. Lemaire O. et al., *Virology* 162, pp. 232–235 (1988)
18. Niesbach-Klösgen U. et al., *Virology* 178, pp. 52–61 (1990)
19. Hehn A. et al., *Virology* 210, pp. 73–81 (1995)
20. Tamada T. et al., *J. Gen. Virol.* 70, pp. 3399–3409 (1989)
21. Kozak M., *J. Cell. Biol.* 108, pp. 299–241 (1989)
22. Pelletier J. & Sonenberg N, *Nature* 334, pp. 320–325 (1988)
23. Tamada T. & Baba T., Annals of the Phytopathological Society of Japan 39, pp. 325–332 (1973)
24. Kuszala M. & Putz C., Annals of Phytopathology 9, pp. 435–446 (1977)
25. Keskin B., *Archiv für Mikrobiology* 49, pp. 348–374 (1964)
26. Asher M. J. C., Rhizomania In The sugar beet crop, ed. D. A. Cooke and R. K. Scott, Chapman & Hall, London, pp. 312–338 (1993)
27. Richard-Molard M., Rhizomanie In Institut francais de la betterave industrielle. Compte-rendu des travaux effectués en 1994, ITB, Paris pp. 225–229 (1995)
28. Henry C. M. et al, *Plant Pathology* 41, pp. 483–489 (1992)
29. Grassi G. et al., *Phytopath. Medit.* 28, pp. 131–139 (1989)
30. Merdinoglu D. et al., *Acad. Agric. Fr.* 79, n° 6, pp. 85–98 (1993)
31. Scolten O. E. et al., *Archives of Virology* 136, pp. 349–361 (1994)
32. Büttenr G. & Bürcky K., Proceedings of the First Symposium of the International Working Group on Plant Viruses with Fungal Vectors, Braunschweig Germany, Aug. 21–24 (1990)
33. Whitney E. D., *Plant Disease* 73, pp. 287–289 (1989)
34. Powell A. P. et al., *Science* 232, pp. 738–743 (1986)
35. Fritchen J. H. & Beachy R. N., *Ann. Rev. Microbiol.* 47, pp. 739–763 (1993)
36. Wilson T. M. A., *Proc. Natl. Acad. Sci. USA* 90, pp. 3134–3141 (1993)
37. Gonsalves D. & Slightom J. L., *Seminars in Virology* 4, pp. 397–405 (1993)
38. D'Halluin K. et al., *Biotechnology* 10, pp. 309–314 (1992)
39. Kallerhof J. et al., *Plant Cell Reports* 9, pp. 224–228 (1990)
40. Ehlers U. et al., *Theoretical and Applied Genetic* 81, pp. 777–782 (1991)
41. Kraus J. et al., Field performance of transgenic sugar beet plants expresing BNYVV coat protein plants, Fourth International Congress of Plant Molecular Biology, Int. Soc. for Plant Molecular Biology, Amsterdam (1994)
42. Maiss E. et al., Proceedings of the Third International Symposium on the Biosafety Results of Field Tests of Genetically Modified Plants and Microorganisms, Monterey, pp. 129–139 (1994)
43. Norris et al., *Plant Molecular Biology* 21, pp. 895–906 (1993)

What is claimed is:

1. A method for inducing resistance to a furovirus comprising a triple gene block 3 sequence with the proviso that it is not the potato virus X, in a plant cell or a plant, comprising:

preparing a nucleic acid construct comprising: a nucleic acid sequence selected from the group consisting of: the nucleic acid sequence corresponding to a triple gene block 3 of said furovirus, its corresponding cDNA, a deletion mutant containing a 3' truncation, wherein said deletion mutant comprises at least 70% of said nucleic acid sequence and wherein said deletion mutant has 30% or fewer of the sequences at its 3' end deleted and retains the activity of said triple gene block 3, or a homolog or mutant wherein said homolog or mutant is 70% homologous to said nucleic acid sequence and wherein said homolog or mutant retains the activity of said triple gene block 3, said nucleic acid construct being operably linked to one or more regulatory sequence(s) active in a plant; and transforming a plant cell with the nucleic acid construct.

2. The method according to claim 1, wherein the nucleic acid sequence of the deletion mutant comprises at least 90% of said nucleic acid sequence and wherein said deletion mutant has 10% or fewer of the sequences at its 3' end deleted and retains the activity of said triple gene block 3, and wherein said homolog or mutant is at least 90% homologous to the nucleic acid sequence of said triple gene block 3 of said furovirus or its corresponding cDNA and wherein said homolog or mutant retains the activity of said triple gene block 3.

3. The method according to claim 1 wherein the furovirus is selected from the group consisting of the apple stem pitting virus, the blueberry scorch virus, the potato virus M, the white clover mosaic virus, the Cymbidium mosaic virus, the barley stripe mosaic virus, the potato mop top virus, the peanut clump virus and the beet soil-borne virus.

4. The method according to claim 1, wherein the plant cell is a stomatal cell.

5. The method according to claim 1, wherein the plant is selected from the group consisting of apple, blueberry, potato, clover, orchid, barley and peanut.

6. The method according to claim 1 wherein the furovirus is BNYVV, the nucleic acid sequence of triple gene block 3 of said virus comprised SEQ ID NO:1 and the plant is a beet.

7. The method according to claim 1, wherein the regulatory sequence comprises a promoter sequence or a terminator sequence active in a plant.

8. The method according to claim 7, wherein the promoter sequence is a constitutive or a foreign vegetal promoter sequence.

9. The method according to claim 7, wherein the promoter sequence is selected from the group consisting of 35S Cauliflower Mosaic Virus promoter, the polyubiquitin Arabidopsis thaliana promoter, and a combination of 35S Cauliflower Mosaic Virus promoter and the polyubiquitin Arabidopsis thaliana promoter.

10. The method according to claim 7, wherein the promoter sequence is a promoter which is mainly active in the root tissue of plants.

11. A transgenic plant resistant to a furovirus with the proviso that it is not the potato virus X, comprising a nucleic acid sequence selected from the group consisting of: the nucleic acid sequence corresponding to a triple gene block 3 of said furovirus, its corresponding cDNA, a deletion mutant containing a 3' truncation, wherein said deletion mutant comprises at least 70% of said nucleic acid sequence and wherein said deletion mutant has 30% or fewer of the sequences at its 3' end deleted and retains the activity of triple gene block 3, or a homolog or mutant wherein said homolog or mutant is 70% homologous to said nucleic acid sequence and wherein said homolog or mutant retains the activity of triple gene block 3, being operably linked to one or more regulatory sequence(s) active in a plant and wherein said homolog or mutant retains the activity of triple gene block 3.

12. The transgenic plant according to claim 11, wherein the nucleic acid sequence of the deletion mutant comprises at least 90% of said nucleic acid sequence and wherein said deletion mutant has 10% or fewer of the sequences at its 3' end deleted and retains the activity of triple gene block 3, and wherein said homolog or mutant is at least 90% homologous to the nucleic acid sequence of triple gene block 3 of said furovirus or its corresponding cDNA and wherein said homolog or mutant retains the activity of triple gene block 3.

13. The transgenic plant according to claim 11, wherein the virus is selected from the group consisting of the apple stem pitting virus, the blueberry scorch virus, the potato virus M, the white clover mosaic virus, the *Cymbidium mosaic* virus, the potato virus X, the barley stripe mosaic virus, the potato mop top virus, the peanut clump virus and the beet soil-borne virus.

14. The transgenic plant according to claim 11, wherein the plant is selected from the group consisting of apple, blueberry, potato, clover, orchid, barley and peanut.

15. The transgenic plant according to claim 11, wherein the transgenic plant is a beet, the virus is BNYVV and the nucleic acid sequence of triple gene block 3 of said virus comprises SEQ ID NO:1.

16. The transgenic plant according to claim 11, wherein the regulatory sequence comprises a promoter sequence and a terminator sequence active in a plant.

17. The transgenic plant according to claim 11, wherein the regulatory sequence(s) comprise a promoter sequence which is a constitutive or a foreign vegetal promoter sequence.

18. The transgenic plant according to claim 17, wherein the promoter sequence is selected from the group consisting of 35S Cauliflower Mosaic Virus promoter, the polyubiquitin Arabidopsis thaliana promoters and a combination of 35S Cauliflower Mosaic Virus promoter and the polyubiguitin Arabidopsis thaliana promoter.

19. The transgenic plant according to claim 17, wherein the promoter sequence is a promoter which is mainly active in root tissues.

20. A transgenic plant tissue selected from the group consisting of fruit, stem, root, tuber, and seed of a plant according to claim 11.

21. The method according to claim 1, additionally comprising regenerating a transgenic plant from the transformed plant cell.

22. The method according to claim 6, wherein the plant is a sugar beet (*Beta vulgaris*).

23. The method according to claim 10, wherein the promoter is the par promoter of the haemoglobin gene from Perosponia andersonii.

24. The transgenic plant according to claim 15, wherein the transgenic plant is a sugar beet (*Beta vulgaris*).

25. The transgenic plant according to claim 19, wherein the promoter is the par promoter of the haemoglobin gene from Perosponia andersonii.

26. The method according to claim 1, wherein the plant is a beet.

* * * * *

SEQUENCE LISTING

```
<160> NUMBER OF SEQ ID NOS: 4

<210> SEQ ID NO 1
<211> LENGTH: 399
<212> TYPE: DNA
<213> ORGANISM: Beet necrotic yellow vein virus (BNYVV)
<220> FEATURE:
<221> NAME/KEY: CDS
<222> LOCATION: (1)...(399)

<400> SEQUENCE: 1

atg gtg ctt gtg gtt aaa gta gat tta tct aat att gta ttg tac ata       48
Met Val Leu Val Val Lys Val Asp Leu Ser Asn Ile Val Leu Tyr Ile
 1               5                  10                  15

gtt gcc ggt tgt gtt gtt gtc agt atg ttg tac tca ccg ttt ttc agc       96
Val Ala Gly Cys Val Val Val Ser Met Leu Tyr Ser Pro Phe Phe Ser
            20                  25                  30
```

-continued

```
aac gat gtt aaa gcg tcc agc tat gcg gga gca att ttt aag ggg agc      144
Asn Asp Val Lys Ala Ser Ser Tyr Ala Gly Ala Ile Phe Lys Gly Ser
        35                  40                  45

ggc tgt atc atg gac agg aat tcg ttt gct caa ttt ggg agt tgc gat      192
Gly Cys Ile Met Asp Arg Asn Ser Phe Ala Gln Phe Gly Ser Cys Asp
    50                  55                  60

att cca aag cat gta gcc gag tcc atc act aag gtt gcc acc aaa gag      240
Ile Pro Lys His Val Ala Glu Ser Ile Thr Lys Val Ala Thr Lys Glu
 65                  70                  75                  80

cac gat gtt gac ata atg gta aaa agg ggt gaa gtg acc gtt cgt gtt      288
His Asp Val Asp Ile Met Val Lys Arg Gly Glu Val Thr Val Arg Val
                85                  90                  95

gtg act ctc acc gaa act att ttt ata ata tta tct aga ttg ttt ggt      336
Val Thr Leu Thr Glu Thr Ile Phe Ile Ile Leu Ser Arg Leu Phe Gly
            100                 105                 110

ttg gcg gtg ttt ttg ttc atg ata tgt tta atg tct ata gtt tgg ttt      384
Leu Ala Val Phe Leu Phe Met Ile Cys Leu Met Ser Ile Val Trp Phe
        115                 120                 125

tgg tat cat aga taa                                                  399
Trp Tyr His Arg
    130


<210> SEQ ID NO 2
<211> LENGTH: 132
<212> TYPE: PRT
<213> ORGANISM: Beet necrotic yellow vein virus (BNYVV)

<400> SEQUENCE: 2

Met Val Leu Val Val Lys Val Asp Leu Ser Asn Ile Val Leu Tyr Ile
 1               5                  10                  15

Val Ala Gly Cys Val Val Val Ser Met Leu Tyr Ser Pro Phe Phe Ser
            20                  25                  30

Asn Asp Val Lys Ala Ser Ser Tyr Ala Gly Ala Ile Phe Lys Gly Ser
        35                  40                  45

Gly Cys Ile Met Asp Arg Asn Ser Phe Ala Gln Phe Gly Ser Cys Asp
    50                  55                  60

Ile Pro Lys His Val Ala Glu Ser Ile Thr Lys Val Ala Thr Lys Glu
65                  70                  75                  80

His Asp Val Asp Ile Met Val Lys Arg Gly Glu Val Thr Val Arg Val
                85                  90                  95

Val Thr Leu Thr Glu Thr Ile Phe Ile Ile Leu Ser Arg Leu Phe Gly
            100                 105                 110

Leu Ala Val Phe Leu Phe Met Ile Cys Leu Met Ser Ile Val Trp Phe
        115                 120                 125

Trp Tyr His Arg
    130


<210> SEQ ID NO 3
<211> LENGTH: 27
<212> TYPE: DNA
<213> ORGANISM: Artificial Sequence
<220> FEATURE:
<223> OTHER INFORMATION: Primer MOV1, sense primer for BNYVV P15 gene.

<400> SEQUENCE: 3

ggtgcttgtg gttaaagtag atttatc                                         27


<210> SEQ ID NO 4
<211> LENGTH: 27
```

-continued

```
<212> TYPE: DNA
<213> ORGANISM: Artificial Sequence
<220> FEATURE:
<223> OTHER INFORMATION: Primer MOV2, antisense primer for BNYVV P15
      gene.

<400> SEQUENCE: 4

ctatgatacc aaaaccaaac tatagac                                       27
```